(12) United States Patent
Cupp et al.

(10) Patent No.: US 7,211,652 B2
(45) Date of Patent: May 1, 2007

(54) PROTEIN FROM HORN FLY SALIVA THAT DISRUPTS HEMOSTASIS

(75) Inventors: Mary S. Cupp, Auburn, AL (US); Dunhua Zhang, Auburn, AL (US); Eddie W. Cupp, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 10/996,248

(22) Filed: Nov. 23, 2004

(65) Prior Publication Data

US 2005/0209143 A1    Sep. 22, 2005

Related U.S. Application Data

(60) Provisional application No. 60/524,752, filed on Nov. 25, 2003.

(51) Int. Cl.
*A61K 38/17* (2006.01)
*C07K 14/435* (2006.01)

(52) U.S. Cl. ................ 530/530; 514/12; 530/858
(58) Field of Classification Search ............... 530/858, 530/350; 514/12
See application file for complete search history.

(56) References Cited

U.S. PATENT DOCUMENTS

| | | | |
|---|---|---|---|
| 5,397,772 | A | 3/1995 | Ribeiro et al. |
| 5,480,864 | A | 1/1996 | Tajima et al. |
| 5,646,115 | A | 7/1997 | Frank et al. |
| 6,162,785 | A | 12/2000 | Cupp et al. |

FOREIGN PATENT DOCUMENTS

| | | |
|---|---|---|
| WO | 98/04795 | 3/1998 |
| WO | WO 00/11172 A | 3/2000 |

OTHER PUBLICATIONS

Revised interim written description guidelines, training materials, Example 13, Protein variants, pp. 50-52, http://www.uspto.gov/web/ offices/pac/writtendesc.pdf.*
Guo et al., "Protein tolerance to random amino acid change," Proc Natl Acad Sci USA 101 (25):9205-9210, 2004.*
Result 1, UniProt database search, alignment of SEQ ID No. 2 and Plasmodium falciparum polypeptide of Gardner et al. (Nature 419:498-511, 2002), GenBank record No. AAN35343, searched on Jan. 17, 2006.*
Abebe, M., et al. "Anticoagulant Activity in Salivary Gland Extracts of Black Flies (Diptera: Simuliidae)," *Journal of Medical Entomology*, 1994, pp. 908-911, vol. 31(6), Entomological Society of America.

(Continued)

*Primary Examiner*—Robert A. Wax
*Assistant Examiner*—Rosanne Kosson
(74) *Attorney, Agent, or Firm*—Alston & Bird LLP

(57) ABSTRACT

Compositions and methods for preventing hematophagous infestation of cattle are provided, directed at isolated proteins that disrupt platelet aggregation. Also provided are nucleotide sequences encoding the proteins. The exemplary haematollogen protein was isolated from the salivary glands of *Haematobia irritans*. The compositions are useful as veterinary vaccines in prevention of blood-feeding in cattle by the infesting horn fly and are also useful in treatment of thrombosis.

7 Claims, 4 Drawing Sheets

```
  1  GAACCATTTCTCTCGAGACATCCCAAGTGATACCTAACACAATTCCTCATAATGGCTATC
                                                             M  A  I   -3
 61  AAAATCTTGACAGTTCTTTTGGTTGTTAGCTGTTTGAGCTATGCCTATGGTTTCAATCCT
      K  I  L  T  V  L  L  V  V  S  C  L  S  Y  A  Y  G  F  N  P   3
121  TTTGGCGCAGGAGGTCTTAGTGTAGACGTCACCGATAAACAATTCAAATGCGACAAGATC
      F  G  A  G  G  L  S  V  D  V  T  D  K  Q  F  K  C  D  K  I  23
181  TCTTGTCCCGCTGATACCGAACGTTGTGTAGTTAGCACGGAAAAAGATCCCAGAAATCCT
      S  C  P  A  D  T  E  R  C  V  V  S  T  E  K  D  P  R  N  P  43
241  AGAATCCTGGCTCACACCAACCTCTGTCTCTCACGCACCGGTTCAGTGTTGGAAAAGAAG
      R  I  L  A  H  T  N  L  C  L  S  R  T  G  S  V  L  E  K  K  63
301  ACATGGTACGAAAGCACCTTTAAAAAGCAAAAGGTTAATGTACACATTGATGCCTATCGC
      T  W  Y  E  S  T  F  K  K  Q  K  V  N  V  H  I  D  A  Y  R  83
361  TATGAAGGAAAATTCACACCTCAAGTTTTAGCAAACAACTGGGATGCCGGAAAAATTGAT
      Y  E  G  K  F  T  P  Q  V  L  A  N  N  W  D  A  G  K  I  D 103
421  GCCGGAAAAACTGCTAAGGAGGACAATGATGCATTCAATAGAGCTGTCGAAGAACTTAGC
      A  G  K  T  A  K  E  D  N  D  A  F  N  R  A  V  E  E  L  S 123
481  AAGAGTTTAGACTTTTAAAATGGAATAAATTCTTTTGTGAAGCGATCGCTTAATATGTTG
      K  S  L  D  F  *                                            128
541  TCATTGTGTAATGAATGCAAATAAATAAATAAAAAAAATCAGCATAACAAAAAAAAAAAA
601  AAAAAAAAAAAAAA
```

(GTGAGTATACACCAAATACCTGATCGCAATTCAGCTGCTTAACTACCACTTTCCATTG TAATTTTCTCACAACACAG)

OTHER PUBLICATIONS

Cross, M. L., et al., "Modulation of murine cellular immune responses and cytokines by salivary gland extract of the black fly Simulium vittatum," *Trop. Med. Parasitol.*, 1994, pp. 119-124, vol. 45, Georg Thieme Stuttgart, New York.

Cross et al., "Differential Modulation of Murine Cellular Immune Responses by Salivary Gland Extract of *Aedes Aegypti*," *Am. J. Trop. Med. Hyg.*, 1994, pp. 690-696, vol. 51(5).

Cupp, E.W., and M.S. Cupp, "Black Fly (Diptera: Simuliidae) Salivary Secretions: Importance in Vector Competence and Disease," *Journal of Medical Entomology*, 1997, pp. 87-94, vol. 34(2), Entomological Society of America.

Cupp, M.S., et al., "Evaluation of a recombinant salivary gland protein (thrombostasin) as a vaccine candidate to disrupt blood-feeding by horn flies," *Vaccine*, 2004, pp. 2285-2297, vol. 22, Elsevier Ltd.

Cupp, M.S., et al., "Horn Fly (Diptera: Muscidae) Saliva Targets Thrombin Action in Hemostasis," *Journal of Medical Entomology*, 2000, pp. 416-421, vol. 37(3), Entomological Society of America.

Cupp, M.S., et al., "Analysis of cDNA and Recombinant Protein for a Potent Vasoactive Protein in Saliva of a Blood-feeding Black Fly, *Simulium Vittatum*," *The Journal of Experimental Biology*, 1998, pp. 1553-1561, vol. 201, The Company of Biologist Limited.

Cupp et al., "Vasodilative Activity in Black Fly Salivary Glands," *Am. J. Trop. Med. Hyg.* 1994, pp. 241-246, vol. 50(2).

Hori, K., et al., "Digestive Enzymes in the Gut and Salivary Gland of the Adult Horn Fly *Haematobia irritans* (Diptera: Muscidae)," *Appl. Ent. Zool.*, 1981, pp. 16-23, vol 16(1).

Hudson, A., "Some Functions of the Salivary Glands of Mosquitoes and other Blood-feeding Insects," *Canadian Journal of Zoology*, 1964, pp. 113-120, vol. 42.

Kerlin, R.L., and P.G. Allingham, "Acquired immune response of cattle exposed to buffalo fly (*Haematobia irritans exigua*)," *Veterinary Parasitology*, 1992, pp. 115-129, vol. 43, Elsevier Science Publishers B.V., Amterdam.

Qureshi et al., "Immunomodulatory Properties of Maxadilan, the Vasodilator Peptide from Sand Fly Salivary Gland Extracts," *Am. J. Trop. Med. Hyg.*, 1996, pp. 665-671, vol. 54(6).

Ribeiro et al., "The Salivary Catechol Oxidase/Peroxidase Activities of the Mosquito *Anopheles Albimanus*," *J. Exp. Biol.*, 1993, pp. 273-287, vol. 179.

Ribiero, J.M.C., "Characterization of a Vasodilator from the Salivary Glands of the Yellow Fever Mosquito *Aedes Aegypti*," *J. Exp. Biol.*, 1992, pp. 61-71, vol. 165.

Ribiero, J.M.C., "Role of Saliva in Blood-feeding by Arthopods," *Ann. Rev. Entomol.*, 1987, pp. 463-478, vol. 32.

Vanhoorelbeke, K., et al., "Inhibition of Platelet Adhesion to Collagen as a New Target for Antithrombotic Drugs," *Current Drug Targets—Cardiovascular & Haematological Disorders*, 2003, pp. 125-140, vol. 3, Bentham Science Publishers Ltd.

Zhang, D., et al., "Thrombostasin: purification, molecular cloning and expression of a novel anti-thrombin protein from horn fly saliva," *Insect Biochemistry and Molecular Biology*, 2002, pp. 321-330, vol. 32, Elsevier Science Ltd.

Zhang, D., et al., "Polymorphism of the thrombostasin gene in the horn fly (*Haematobia irritans*) revealed in a cDNA library and in genomic DNA," *Mol Genet Genomics*, 2001, pp. 296-302, vol. 266.

* cited by examiner

```
1    GAACCATTTCTCTCGAGACATCCCAAGTGATACCTAACACAATTCCTCATAATGGCTATC
                                                          M  A  I   -3
61   AAAATCTTGACAGTTCTTTTGGTTGTTAGCTGTTTGAGCTATGCCTATGGTTTCAATCCT
     K  I  L  T  V  L  L  V  V  S  C  L  S  Y  A  Y  G  F  N  P    3
121  TTTGGCGCAGGAGGTCTTAGTGTAGACGTCACCGATAAACAATTCAAATGCGACAAGATC
     F  G  A  G  G  L  S  V  D  V  T  D  K  Q  F  K  C  D  K  I    23
181  TCTTGTCCCGCTGATACCGAACGTTGTGTAGTTAGCACGGAAAAAGATCCCAGAAATCCT
     S  C  P  A  D  T  E  R  C  V  V  S  T  E  K  D  P  R  N  P    43
241  AGAATCCTGGCTCACACCAACCTCTGTCTCTCACGCACCGGTTCAGTGTTGGAAAAGAAG
     R  I  L  A  H  T  N  L  C  L  S  R  T  G  S  V  L  E  K  K    63
301  ACATGGTACGAAAGCACCTTTAAAAAGCAAAAGGTTAATGTACACATTGATGCCTATCGC
     T  W  Y  E  S  T  F  K  K  Q  K  V  N  V  H  I  D  A  Y  R    83
361  TATGAAGGAAAATTCACACCTCAAGTTTTAGCAAACAACTGGGATGCCGGAAAAATTGAT
     Y  E  G  K  F  T  P  Q  V  L  A  N  N  W  D  A  G  K  I  D    103
421  GCCGGAAAAACTGCTAAGGAGGACAATGATGCATTCAATAGAGCTGTCGAAGAACTTAGC
     A  G  K  T  A  K  E  D  N  D  A  F  N  R  A  V  E  E  L  S    123
481  AAGAGTTTAGACTTTTAAAATGGAATAAATTCTTTTGTGAAGCGATCGCTTAATATGTTG
     K  S  L  D  F  *                                               128
541  TCATTGTGTAATGAATGCAAATAAATAAATAAAAAAAATCAGCATAACAAAAAAAAAAAA

601  AAAAAAAAAAAAA (GTGAGTATACACCAAATACCTGATCGCAATTCAGCTGCTTAACTACCACTTTCCATTG
     TAATTTTCTCACAACACAG)
```

FIG. 1

PROTEIN FROM HORN FLY SALIVA THAT DISRUPTS HEMOSTASIS

CROSS-REFERENCE TO RELATED APPLICATION

This application claims the benefit of U.S. Provisional Application No. 60/524,752, filed Nov. 25, 2003, which is hereby incorporated herein in its entirety by reference.

FEDERALLY SPONSORED RESEARCH OR DEVELOPMENT

The research underlying this invention was supported in part with funds from USDA Grant No. USDA-96-35302-3381. The United States Government may have an interest in the subject matter of this invention.

FIELD OF THE INVENTION

The invention relates to veterinary vaccines for prevention of hematophagous infestation of cattle and medical treatment of thrombosis.

BACKGROUND OF THE INVENTION

Losses in livestock production in the United States due to ectoparasite infestations have been estimated to exceed $2.26 billion annually (Byford et al. (1992) *J. Anim. Sci.* 70:597–602). Of the five to six major arthropod pest species involved, the horn fly *Haematobia irritans linnaeus* is the most significant and widespread. Its annual economic impact on cattle production in the U.S.A. has been estimated at $730.3 million. In Canada, control of this ectoparasite in cattle production has been estimated to reduce losses by $71–107 million per year using 1977 dollar values (Haufe and Weintraub (1985) *Can. Entomol.* 117: 901–907). Thus, in North America, the annual economic impact on cattle production by this blood-sucking fly approaches $1 billion.

Physiological manifestations of hornfly infestation include an increase in heart rates, respiration rates, and rectal temperatures. Additionally, water consumption and urine production are significantly increased as well as urinary nitrogen secretion. Blood cortisol concentrations are also significantly increased. Decreased weight gain, increased activity, and decreased grazing have also been reported. (Schwinghammer et al. (1986) *J. Econ. Entomol.* 79: 1010–1014).

The adult stage of both sexes of *H. irritans* are obligate ectoparasites that feed on blood intermittently during the 24 hours of the day. Unlike other dipterous pests that are transient blood-feeders (such as black flies, mosquitoes, horse flies, and stable flies), the winged adults of *H. irritans* remain on the bovine host and, when needing nourishment, recurrently insert their mouthparts into the skin to feed. Harris et al. ((1974) *Ann. Entomol. Soc. Am.* 67: 891–894) noted that under experimental conditions, female horn flies spent an average of 163 minutes per day feeding; males averaged 96 minutes per day. Each female ingested an average of 17.1 mg of blood per day while males imbibed 12.1 mg per day per individual due to the difference in feeding times (Harris and Frazer (1970) *Ann. Entomol. Soc. Am.* 63: 1475–1476).

The scientific literature describing the salivary gland physiology of *H. irritans*, particularly with reference to blood-feeding, is sparse. Hori et al. ((1981) *Appl. Ent. Zool.* 16: 16–23) compared several categories of digestive enzymes in the gut and salivary glands of *H. irritans* with *Stomoxys calcitrans* (Linnaeus), the stable fly. Weak aminopeptidase activity was detected in *H. irritans* saliva, suggesting that proteases and glycosidases in the gut are exclusively responsible for digestion of blood.

The horn fly *Haematobia irritans linnaeus* is a subspecies with *H. i. exigua de Meijere*, the buffalo fly that occurs in Australia and elsewhere in the southern hemisphere. Kerlin and Hughes ((1992) *Med. Vet. Entomol.* 6: 121–126) have compared enzymes in the saliva of four parasitic arthropods (*H. irritans exigua*, *Boophilus microplus* (Canestrini), *Aedes aegypti* (Linnaeus), and *Lucilia cuprina* (Wiedemann)) and noted differences in enzyme profiles of saliva between the four species that apparently reflect their dissimilar feeding strategies. These differences were mainly in the type and levels of glycosidase and protease activities. *H. irritans exigua* saliva, collected by serotonin stimulation and then evaluated by SDS polyacrylamide gel electrophoresis, produced 7–8 bands by silver staining. Apyrase activity in saliva and salivary gland extracts (SGEs) of this species was marginally detectable, suggesting that this subspecies does not prevent bovine platelet aggregation in the same way as many other blood-feeding arthropods (Ribeiro (1987) *Ann. Rev. Entomol.* 32: 463–478).

Furthermore, investigation of immune response of cattle exposed to *H. irritans exigua* showed production of high levels of circulating antibodies to some but not all of the buffalo fly antigens; nevertheless, flies feeding on previously exposed cattle did not exhibit higher mortality than those fed on unexposed cattle. (Kerlin and Allingham (1992) *Vet. Parasitol.* 43: 115–129).

Elucidation of biochemical strategies adopted by blood-feeding arthropods has advanced in the past decade. Although the presence of anticoagulants in saliva of hematophagous arthropods has been known for at least eight decades, only recently have some of the active components been purified and their molecular structures defined. It has become apparent that coagulation factors such as factors Xa and thrombin (factor II), which occur at a nexus in the coagulation cascade, are frequently targeted.

Studies of saliva from several species of black flies have suggested that specific enzyme targets may be associated with host selection (Abebe et al. (1994) *J. Med. Entomol.* 31: 908–911). For example, data for zoophagic species that prefer cattle indicate that thrombin is an important target molecule whose inactivation may also prevent irreversible platelet aggregation in addition to impeding the coagulation cascade. See Hudson (1964) *Can. J. Zool.* 42: 113–120, for *Stomoxys calcitrans*; and Parker and Mant (1979) *Thrombos. Haemostas (Stuttg.)* 42: 743–751, on *G. morsitans* (Westwood) saliva.

Because of the adverse impact of the above-described ectoparasitic infestation in cattle, there is a therapeutic and economic need for preventing such infestation.

There is also need for treatment of thromboembolic diseases. Thromboembolic diseases are among the most important circulatory diseases. A thrombus is a blood clot that partially or completely blocks blood flow through a blood vessel. An embolus is a thrombus that has formed elsewhere in the body, broken free, and traveled to the site where blockage occurs. Blockage in the brain results in a stroke, i.e., a cerebral infarction, which is a localized area of necrosis. An embolus in a lung can produce pulmonary embolism, one of the principal lung diseases in bed-ridden patients. Bed ridden and elderly persons are also particularly prone to thrombophlebitis, which is a blockage of circulation in a leg caused by an embolus. An embolus or thrombus lodging in one of the blood vessels serving the heart causes necrosis of part of the heart tissue, or a myocardial infarction, commonly called a heart attack.

The initiating event of many myocardial infarctions is the hemorrhage into atherosclerotic plaques. Such hemorrhage often results in the formation of a thrombus (or blood clot) in the coronary artery which supplies the infarct zone. This thrombus is composed of a combination of fibrin and blood platelets. The formation of a fibrin-platelet clot has serious clinical ramifications. The degree and duration of the occlusion caused by the fibrin-platelet clot determines the mass of the infarct zone and the extent of damage.

The formation of fibrin-platelet clots in other parts of the circulatory system may be partially prevented through the use of anticoagulants, such as heparin. Unfortunately, heparin has not been found to be universally effective in preventing reocclusion in myocardial infarction victims in which the degree of blood vessel occlusion is greater than or equal to 70%, particularly in those patients with severe residual coronary stenosis. Among the more promising of the agents are hirudin and its analogs, which bind to and inactivate thrombin. Hirudin has a theoretical advantage over heparin as an anti-thrombotic agent. Thrombin bound to thrombi or platelets is relatively protected from inhibition by heparin while hirudin, at least in vitro, is still effective. Other promising investigational agents include fibrinogen receptor antagonists, which block platelet aggregation and dense granule release by a mechanism distinct from that of aspirin, and inhibitors of thromboxane production.

There is therefore a need for additional antithrombin agents which exhibit low toxicity, little or no antigenicity, and a very short clearance time from circulation.

SUMMARY OF THE INVENTION

Isolated haematollogen proteins having antihemostatic activity are provided, as are nucleotide sequences encoding them. The exemplary haematollogen protein was isolated from the salivary glands of *Haematobia irritans*, the blood-feeding horn fly. The provided proteins and nucleotides are particularly useful as veterinary vaccines in prevention of blood-feeding (haematophagy) in cattle by the infesting horn fly. The proteins of the invention are also useful in the prevention and/or treatment of thrombosis and conditions in which platelet aggregation is undesirable. Methods of administering the proteins and nucleotide sequences of the invention are also provided.

BRIEF DESCRIPTION OF THE DRAWINGS

FIG. 1 shows the haematollogen nucleotide sequence and deduced amino acid sequence. The translation initiation codon (ATG), stop codon (TAA), and polyadenylation site (AATAAA) are in bold font. The putative secretion signal peptide is shown in italic font, and the location of the intron in genomic haematollogen is indicated by an arrow. The sequence of the intron itself is shown in parentheses.

DETAILED DESCRIPTION OF THE INVENTION

Figure 2:
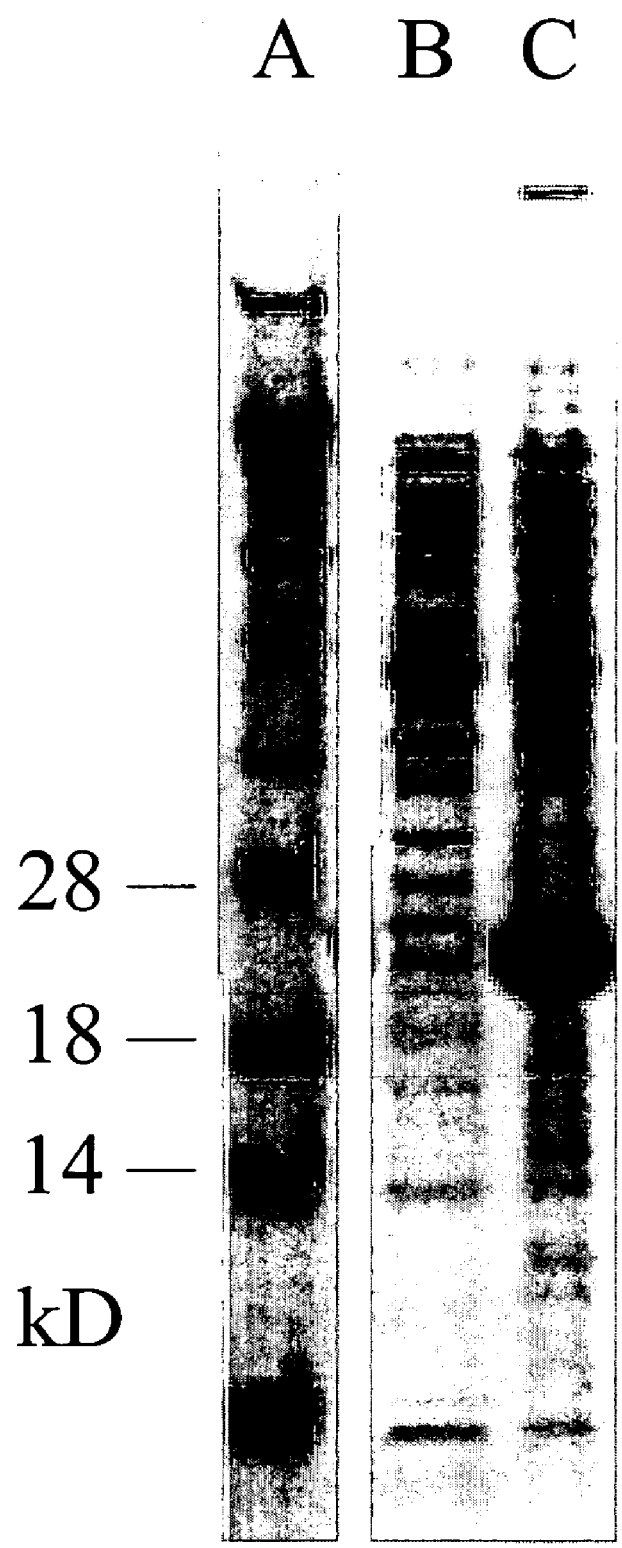
FIG. 2 shows an SDS-PAGE gel of recombinant haematollogen preparations from uninduced (lane B) and IPTG-induced (lane C) *E. coli*. Markers are shown in lane A.

Methods and compositions for preventing hematophagy (blood-feeding) in cattle are provided. The methods and compositions also find use in the treatment of thrombosis in a mammal as well as in the treatment of conditions in which decreased platelet aggregation and/or activation are advantageous. See, e.g., Vanhoorelbeke et al. (2003) *Current Drug Targets—Cardiovascular & Haemotological Disorders* 3: 125–140. The compositions comprise protein from the salivary gland of the hematophagous horn fly *Haematobia irritans*, which belongs to the suborder Cyclorrhapha of the order Diptera (see, e.g., Yeates et al. (1999) *Annu. Rev. Entomol.* 44: 397–428). The major function of the protein, which has been designated haematollogen, is to prevent coagulation of blood by disrupting the aggregation of platelets, which is referred to herein as "antihemostatic activity." While the invention is not bound by a particular mechanism of action, it is believed that haematollogen functions by disrupting platelet aggregation induced by exposure to collagen.

Compositions of the invention include the exemplary proteins the amino acid sequences of which are set forth in SEQ ID NO:2 and SEQ ID NO:4 and that are involved in disrupting and/or decreasing platelet aggregation. In particular, the present invention provides for isolated polynucleotides comprising nucleotide sequences encoding the amino acid sequences shown in SEQ ID NO:2 and SEQ ID NO:4. Further provided are polypeptides having an amino acid sequence encoded by a polynucleotide described herein, for example those set forth in SEQ ID NO:1 and SEQ ID NO:3, and fragments and variants thereof.

By "hematophagy" is intended feeding on the blood of a host organism by another organism. By "hematophagous infestation" is intended a host-parasite relationship comprising feeding on the blood of the host by the parasite. By "thrombosis" is intended the formation, development or presence of a thrombus. By "disrupting platelet aggregation" is intended that the normal aggregation process of platelets is interfered with so that aggregation is measurably diminished. That is, by "disrupting platelet aggregation" is intended that platelet aggregation is decreased by at least 5%, 10%, 15%, 20%, 25%, 30%, 40%, 50%, 60%, 70%, 80%, 90%, 100%, 200%, 300%, 400%, 500%, or more when compared to an appropriate control, for example, platelet aggregation where no haematollogen is present. Platelet aggregation can be measured using methods known in the art. See, for example, Krause et al. (2001) *Platelet* 12: 423–430.

Substantially purified preparations of haematollogen are provided. Such substantially purified preparations include proteins substantially free of any compound normally associated with the protein in its natural state. Such proteins can be assessed for purity by SDS-PAGE, chromatography, electrophoresis or other methods. See, M. P. Deutscher (ed.), *Guide to Protein Purification*, Academic Press, Inc. (1990).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. The terms "substantially pure" or "substantially purified" are not meant to exclude artificial or synthetic mixtures of the protein or polynucleotide with other compounds. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotide may encode protein fragments that retain the biological activity of the native protein and hence disrupt platelet aggregation. For example, a protein consisting of the amino acid sequence set forth in SEQ ID NO:2 (i.e., mature hematollogen protein), which is encoded by a polynucleotide consisting of the nucleotide sequence set forth in SEQ ID NO:1, is a fragment of a protein consisting of the amino acid sequence set forth in SEQ ID NO:3, which is encoded by a polynucleotide consisting of the nucleotide sequence set forth in SEQ ID NO:4. Alternatively, fragments of a polynucleotide that are useful as hybridization probes generally do not encode fragment proteins that retain biological activity. Thus, fragments of a nucleotide sequence may range from at least about 20 nucleotides, about 50 nucleotides, about 100 nucleotides, and up to the length of a polynucleotide encoding a protein of the invention.

A fragment of a haematollogen polynucleotide that encodes a biologically active portion of a haematollogen protein of the invention will encode at least 10, 20, 30, 40, 50, 60, 70, 80, 90, 100, 110, 120, or 125 contiguous amino acids, or up to the total number of amino acids present in a haematollogen protein of the invention (for example, 128 amino acids for SEQ ID NO: 2). Fragments of a haematollogen polynucleotide that are useful as hybridization probes or PCR primers generally need not encode a biologically active portion of a haematollogen protein.

Thus, a fragment of a haematollogen polynucleotide may encode a biologically active portion of a haematollogen protein, or it may be a fragment that can be used as a hybridization probe or PCR primer using methods disclosed below. A biologically active portion of a haematollogen protein can be prepared by isolating a portion of one of the haematollogen polynucleotides of the invention, expressing the encoded portion of the haematollogen protein (e.g., by recombinant expression in vitro), and assessing the activity of the encoded portion of the haematollogen protein. Polynucleotides that are fragments of a haematollogen nucleotide sequence comprise at least 16, 20, 50, 75, 100, 150, 200, 250, 300, 350, or 360 contiguous nucleotides, or up to the number of nucleotides present in a haematollogen polynucleotide disclosed herein (for example, 384 nucleotides for SEQ ID NO:1).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the haematollogen polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis, but which still encode a haematollogen protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO:2 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active; that is they continue to possess the desired biological activity of the native protein, i.e., the activity of disrupting platelet aggregation as described herein. Such variants may result from, for example, genetic polymorphism or from human manipulation. Biologically active variants of a native haematollogen protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the haematollogen proteins can be prepared by mutations in the DNA. Methods for mutagenesis and polynucleotide alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired activity of disrupting platelet aggregation. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by an aggregometer assay known in the art. For example, the activity can be evaluated by the microtiter plate method of Krause et al. (2001) *Platelet* 12: 423–430, herein incorporated by reference; see also Rand et al. (2003) *Transfusion and Apheresis Science* 28: 307–317 for other suitable methods.

Variant polynucleotides and proteins also encompass sequences and proteins derived from a mutagenic and recombinogenic procedure such as DNA shuffling. With such a procedure, one or more different haematollogen coding sequences can be manipulated to create a new haematollogen possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a haematollogen gene of the invention and other known haematollogen genes to obtain a new gene coding for a protein with an improved property of interest, such as an increased Km in the case of an enzyme. Strategies for such DNA shuffling are known in the art. See, for example, Stemmer (1994) *Proc. Natl. Acad. Sci. USA* 91: 10747–10751; Stemmer (1994) *Nature* 370: 389–391; Crameri et al. (1997) *Nature Biotech.* 15:436–438; Moore et al. (1997) *J. Mol. Biol.* 272: 336–347; Zhang et al. (1997) *Proc. Natl. Acad. Sci. USA* 94: 4504–4509; Crameri et al. (1998) *Nature* 391: 288–291; and U.S. Pat. Nos. 5,605,793 and 5,837,458.

The polynucleotides of the invention can be used to isolate corresponding sequences from other organisms, particularly other hematophagous insects. In this manner, methods such as PCR, hybridization, and the like can be used to identify such sequences based on their sequence homology to the sequences set forth herein. Sequences isolated based on their sequence identity to the haematollogen sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that disrupt platelet aggregation and which hybridize under stringent conditions to the haematollogen sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the haematollogen polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire haematollogen polynucleotide disclosed herein, or one or more portions thereof, may be used as a probe capable of specifically hybridizing to corresponding haematollogen polynucleotide and messenger RNAs. To achieve specific hybridization under a variety of conditions, such probes include sequences that are unique among haematollogen polynucleotide sequences and are optimally at least about nucleotides in length, and most optimally at least about 20 nucleotides in length. Such probes may be used to amplify a corresponding haematollogen polynucleotide from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background, or at least 3-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium and is typically about, for example, about 15 minutes, one hour, or two hours in length.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); and low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes, Part I*, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local alignment algorithm of Smith et al. (1981) *Adv. Appl. Math.* 2:482; the global alignment algorithm of Needleman and Wunsch (1970) *J. Mol. Biol.* 48:443–453; the search-for-local alignment method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif. USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff(1989) *Proc. Natl. Acad. Sci. USA* 89: 10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The haematollogen polynucleotide of the invention can be provided in expression cassettes for expression in the organism of interest. The cassette will include 5' and 3' regulatory sequences operably linked to a haematollogen polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the haematollogen polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter) and a haematollogen polynucleotide of the invention. The regulatory regions (i.e., promoters, transcriptional regulatory regions, and translational termination regions) and/or the haematollogen polynucleotide of the invention may be native/analogous to the host cell or to each other. Alternatively, the regulatory regions and/or the haematollogen polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

While it may be optimal to express the sequences using heterologous promoters, the native promoter sequences may be used. Such constructs can change expression levels of haematollogen in a cell, thereby altering the phenotype of the cell, organ, or organism in which they are expressed.

Where appropriate, the polynucleotides may be optimized for increased expression in the transformed organism. That is, the polynucleotides can be synthesized using bacterial-preferred codons or animal-preferred codons for improved expression. Methods for optimizing polynucleotides in this manner are well-known in the art. Additional sequence modifications are known to enhance gene expression in a cellular host. For example, the G-C content of the sequence may be adjusted to levels average for a given cellular host, as calculated by reference to known genes expressed in the host cell. These modifications are contemplated in the practice of the invention.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Thus, once the nucleotide sequence of haematollogen is identified as disclosed herein, those skilled in the art can produce large quantities of the protein for therapeutic use. Accordingly, recombinant protein and methods for producing the recombinant protein are encompassed by the present invention. In this manner, the nucleotide sequence encoding the haematollogen protein can be utilized in vectors for expression in various types of host cells, including both prokaryotes and eukaryotes, to produce large quantities of the protein, or active analogues, or fragments thereof, and other constructs capable of producing a protein that disrupts platelet aggregation.

Generally, methods for the expression of recombinant DNA are known in the art. See, for example, Sambrook et al. *Molecular Cloning*, Cold Spring Harbor Laboratory (1989). Additionally, host cells and expression vectors, such as a baculovirus expression vector, may be employed in carrying out the present invention, as is known in the art and described, for example, in U.S. Pat. Nos. 4,745,051 and 4,879,236. In general, a baculovirus expression vector comprises a baculovirus genome containing the gene to be expressed inserted into the polyhedron gene at a position ranging from the polyhedron transcriptional start signal to the ATG start site and under the transcriptional control of a baculovirus polyhedron promoter.

The polypeptides of the invention may be subject to one or more post-translational modifications such as sulfation, COOH-amidation, acylation or chemical alteration of the polypeptide chain. The polynucleotide encoding the haematollogen protein may be constructed to also comprise a leader peptide that is capable of directing secretion of the polypeptide from cells in which the polypeptide is expressed. The polynucleotide encoding the leader peptide is typically fused to the 5'-end of the polynucleotide encoding the polypeptide of interest. Leader sequences are known in the art and include the OmpA leader peptide as well as the leader peptide of vesicular stomatitis virus G protein (VSV G protein). The OmpA leader is useful when expression is in a bacterial host, such as *E. coli*, while the VSVG protein is useful when expression is in insect cells.

The polynucleotide may comprise a nucleotide sequence that encodes a cleavable site to release the polypeptide of the invention, and/or may comprise a nucleotide sequence which encodes a carrier polypeptide sequence fused via a cleavable linkage to the N-terminus of a polypeptide of the invention. The cleavable linkage may be one cleavable by cyanogen bromide.

A broad variety of suitable prokaryotic and microbial vectors are available for expression of the haematollogen proteins of the invention in a variety of hosts including other organisms, including microorganisms. Likewise, the promoters and other regulatory agents used in expression of foreign proteins are available in the art. Promoters commonly used in recombinant microbial expression vectors are known in the art and include the beta-lactamase (penicillinase) and lactose promoter systems (Chang et al. (1978) *Nature* 275: 615 and Goeddel et al. (1979) *Nature* 281: 544); a tryptophan (TRP) promoter system (Goeddel et al. (1980) *Nucleic Acids Res.* 8: 4057); and the Tac promoter (DeBoer et al. (1983) *Proc. Natl. Acad. Sci. U.S.A.* 80: 21). While these are commonly used, other microbial promoters are available. Details concerning nucleotide sequences of many have been published, enabling a skilled worker to operably ligate them to DNA encoding the protein in plasmid or viral vectors. See, for example, Siedenlist et al. (1980) *Cell* 20: 269.

Eukaryotic host cells such as yeast may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al. (1979) *Nature* 282: 9; Kingsman et al. (1979) *Gene* 7: 141; Tschemper et al. (1980) *Gene* 10: 157). This plasmid contains the trp1 gene, which provides a selection marker for a mutant strain of yeast lacking the ability to grow in tryptophan, for example ATCC No. 44076 or PEP4-1 (Jones (1977) *Genetics* 85: 12). The presence of the trp1 lesion in the yeast host cell genome then provides an effective environment for detecting transformation by growth in the absence of tryptophan.

Suitable promoter sequences for use in yeast vectors include the promoters for metallothionein, alcohol dehydrogenase, adenylate cyclase, 3-phosphoglycerate kinase (Hitzeman et al. (1980) *J. Biol. Chem.* 255: 2073) and other glycolytic enzymes (Hess et al. (1968) *J. Adv. Enzyme Reg.* 7: 149; and Holland et al. (1978) *Biochemistry* 17: 4900) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

The invention provides antibody preparations that selectively bind the proteins of the invention, or any variants or fragments thereof as described. An antibody is considered to selectively bind, even if it also binds to other proteins that are not substantially homologous with the haematollogen protein. These other proteins share homology with a fragment or domain of the haematollogen protein giving rise to antibodies that bind to both proteins by virtue of the homologous sequence. In this aspect, it is recognized that antibody binding to the haematollogen protein is still selective.

Antibody preparations encompass monoclonal or polyclonal antibodies, intact antibodies or fragments thereof (e.g., Fab), purified preparations such as affinity-purified preparations, or less pure preparations such as ascites fluid, sera and the like. Methods for raising antibodies are well known in the art and include but are not limited to those described in Harlow and Lane ((1988) Antibodies, A Laboratory Manual, Cold Spring Harbor Laboratory Press), the contents of which are herein incorporated by reference. The invention also embodies antibody preparations which neutralize biological functions of the provided proteins, variants or fragments thereof. Such functions include but are not limited to antihemostatic activity. The invention also provides compositions capable of modulating the immune response. By modulating the immune response is intended a determinable change in the immune system of a host organism effected by administering the herein described compositions of the invention to that host.

The compositions of the present invention find therapeutic use as veterinary vaccines in treatment of hematophagy in a mammal. The methods comprise administering to the mammal a veterinary vaccine comprising a therapeutically effective amount of the compositions of the invention. In this aspect, a therapeutically effective amount is that amount which results in a detectable reduction, amelioration, elimination or prevention of hematophagous infestation in the mammal to which the vaccine of the present invention was administered. For example, the working examples provided herein demonstrate the therapeutic effectiveness of the compositions of the invention for ameliorating hematophagous infestation by decreasing ovariole number in infesting flies (see Example 4).

While the vaccines of the invention can be used with any mammal, of particular interest are livestock, more particularly, cattle, horses, and the like. The compositions are useful for vaccination against the hematophagous fly of the sub-order Cyclorrhapha, more particularly of the species *Haematobia irritans*. However, the invention finds use as a vaccination against any hematophagous organism where a vaccination using compositions and methods of the present invention is therapeutically effective. The invention may be used in conjunction with other compositions and methods in providing a vaccine; for example, proteins of the invention may be used in a vaccine with antithrombin proteins known in the art, such as those taught in U.S. Pat. No. 6,162,785. By "antithrombin activity" is intended a biological activity that reduces or eliminates the procoagulant action of thrombin; and/or inhibits thrombosis.

For veterinary applications, the compositions of the invention can be formulated into any acceptable pharmaceutical preparation as described below or any other acceptable preparation for veterinary use.

In some embodiments, the vaccines comprise the nucleotide compositions of the invention as described herein. As described by Cox et al. (1993) *J. Virol.* 67: 5664–5667; Fynan et al. (1993) *Proc. Natl. Acad. Sci. USA* 90: 11478–11482; and Lewis et al. (1997) *Vaccine* 15: 861–864; and reviewed by Robinson (1997) *Vaccine* 15: 785–787; and Tighe et al. (1998) *Immunol. Today* 19: 89–97, the contents of all of which are herein incorporated by reference, nucleic acid vaccines can be readily constructed and produced. In general, target DNA sequences encoding the protein to be used as an immunogen are cloned into eukaryotic expression vectors which are then transformed into appropriate host bacteria. Plasmid DNA is then purified from the bacteria and then directly injected into the animal where its expression by cells in the inoculated host produces the target protein, thereby raising an immune response. Injection of the DNA is generally by intramuscular injection, but may also be by another suitable method such as intradermal injection. See, for example, Cox et al. (1993) *J. Virol.* 67: 5664–5667, herein incorporated by reference. Nanogram levels of protein expressed from such DNA may be utilized to stimulate an immune response and protect against infectious agents achieved by skin, muscle and intravenous inoculations of DNA. See, for example, Fynan et al. (1993) *Proc. Natl. Acad. Sci. USA* 90: 11478–11482; Cox et al. (1993) *J. Virol.* 67: 5664–5667, herein incorporated by reference. Such plasmids introduced by intramuscular or intradermal injection stimulate a protective response that abrogates clinical disease following challenge.

The compositions of the present invention can be formulated into pharmaceutical preparations for therapeutic use. Such compositions find use in the treatment of medical conditions related to clotting, such as, for example, venous thrombosis, vascular shunt occlusion and thrombin-induced disseminated intravascular coagulation. A composition of the invention is therapeutically useful; that is, a composition of the invention, when administered to a mammal in need of treatment, causes an improvement in a medical condition related to clotting. In some embodiments, the improvement in the medical condition would result from a decrease in platelet aggregation. The compositions of the invention can be used alone or in combination with other antithrombin and therapeutic agents, including veterinary agents. For example, the compositions of the invention can be used in combination with the antithrombin and therapeutic agents disclosed in U.S. Pat. No. 6,162,785. Other agents are known in the art.

The antihemostatic compositions can be formulated according to known methods to prepare pharmaceutically useful compositions, such as by admixture with a pharmaceutically acceptable carrier vehicle. Suitable vehicles and their formulation are described, for example, in Remington's Pharmaceutical Sciences 19th ed., Osol, A. (ed.), Mack Easton Pa. (1980). In order to form a pharmaceutically acceptable composition suitable for effective administration, such compositions will contain an effective amount of the haematollogen protein, either alone, or with a suitable amount of carrier vehicle.

Additional pharmaceutical methods may be employed to control the duration of action. Controlled release preparations may be achieved by the use of polymers to complex or absorb the compositions. The controlled delivery may be exercised by selecting appropriate macromolecules (for example, polyesters, polyamino acids, polyvinyl pyrrolidone, ethylene-vinylacetate, methylcellulose, carboxymethylcellulose, or protamine sulfate). The rate of drug release may also be controlled by altering the concentration of such macromolecules.

Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly(methylmethacrylate) microcapsules, respectively, or in a colloid drug delivery system, for example, liposomes, albumin, microspheres, microemulsions, nanoparticles, nanocapsules, or in macroemulsions. Such teachings are disclosed in Remington's Pharmaceutical Sciences (1980).

In more specific embodiments, a polypeptide of the invention may be converted into a pharmaceutically acceptable salt. It may be converted into an acid additional salt with an organic or inorganic acid. Suitable acids include acetic, succinic and hydrochloric acid. Alternatively, the peptide may be converted into a carboxylic acid salt such as the ammonium salt or an alkali metal salt such as the sodium or potassium salt.

A polypeptide or pharmaceutically acceptable salt thereof may be used in a pharmaceutical composition, together with a pharmaceutically acceptable carrier or excipient therefore.

Such a formulation is typically for intravenous administration (in which case the carrier is generally sterile saline or water of acceptable purity). A polypeptide can therefore be used for the therapy and prophylaxis of thrombosis and thromboembolisms in a human or other mammal, including the prophylaxis of post-operative thrombosis, for acute shock therapy (for example for septic or polytraumatic shock), for the therapy of consumption coagulopathics, in hemodialyses, haemoseparations and in extracorporeal blood circulation. In one embodiment of the invention, the polypeptide or salt thereof can be coadministered with a plasminogen activator, such as tissue plasminogen activator.

The dosage depends especially on the specific form of administration and on the purpose of the therapy or prophylaxis. The size of the individual doses and the administration regime can best be determined by way of an individual judgment of the particular case of illness; the methods of determining relevant blood factors required for this purpose are familiar to the person skilled in the art. Normally, in the case of an injection the therapeutically effective amount of the compounds according to the invention is in a dosage range of from approximately from 0.005, 0.01, 0.02, 0.05, or 0.1 mg/kg body weight to approximately 0.15, 0.2, 0.3, 0.5, 0.7, 1.0, 2.0, or 5.0 mg/kg body weight, or from approximately 0.1 to approximately 0.2 mg/kg body weight.

The administration is effected by intravenous, intramuscular or subcutaneous injection. Accordingly, pharmaceutical compositions for parenteral administration in single dose form contain per dose, depending on the mode of administration, from approximately 0.4 to approximately 7.5 mg of the compound according to the invention. In addition to the active ingredient these pharmaceutical compositions usually also contain a buffer, for example a phosphate buffer, which is intended to keep the pH value between approximately 3.5 and 7, and also sodium chloride, mannitol or sorbitol for adjusting the isotonicity. The preparations may be freeze-dried or dissolved. An antibacterially active preservative may be included, for example from 0.2 to 0.3% 4-hydroxybenzoic acid methyl ester or ethyl ester.

A composition for topical application can be in the form of an aqueous solution, lotion or gel, an oily solution or suspension or a fat-containing or, especially, emulsified ointment. A composition in the form of an aqueous solution is obtained, for example, by dissolving the active ingredients according to the invention, or a therapeutically acceptable salt thereof, in an aqueous buffer solution of from e.g., pH 4 to pH 6.5 and, if desired, adding a further active ingredient, for example an anti-inflammatory agent, and/or a polymeric binder, for example polyvinylpyrrolidone, and/or a preservative. The concentration of active ingredients is from approximately 0.1 to approximately 1.5 mg, preferably from 0.25 to 1.0 mg, in 10 ml of a solution or 10 g of a gel.

In addition to the compositions described above and pharmaceutical compositions analogous thereto that are intended for direct medicinal use in the body of a human or a mammal, the present invention relates also to pharmaceutical compositions and preparations for medicinal use outside the living body of humans or mammals. Such compositions and preparations are used especially as antihemostatic additives to blood that is being subjected to circulation or treatment outside the body (for example haemoseparation). Such preparations, such as stock solutions or alternatively preparations in single dose form, are similar in composition to the injection preparations described above; however, the amount of concentration of active ingredient is advantageously based on the volume of blood to be treated or, more precisely, on its thrombin content. Depending on the specific purpose, the suitable dose is from approximately 0.01 to approximately 0.2 mg of the active ingredient/liter of blood, although the upper limit may still be exceeded without risk as the agent is harmless even in relatively high amounts.

EXPERIMENTAL

Example 1—Isolation of Haematillogen Protein

Collection and Rearing of *H. irritans*

Pupae were shipped from the U.S.D.A. Livestock Insects Research Laboratory in Kerrville, Tex., on a biweekly basis and stored at 4° C. until needed. They were removed and placed in cardboard cartons, modified from pint-sized ice cream cartons (Neptune Paper Products, Inc., Newark, N.J.) in an incubator set at 27° C. with 16:8 hours (L:D) to promote emergence of adults. An absorbent cotton pad was placed on top of each cage and used as a wick to supply water to adults until time of experimentation, between 24–48 hours post-emergence.

Wild-caught adults collected from the University of Arizona dairy herd and from the Auburn University beef and dairy herds were used for some assays. They were transported to the laboratory within an hour of collection and maintained as above prior to experimentation.

Recovery of Salivary Glands

Both sexes of *H. irritans* are obligate blood feeders and their salivary glands are similar in morphology and location in the body to stable flies (*Stomoxys calcitrans*) and tsetse flies (*Glossina* spp.) The following protocol was used for dissection of glands: (a) the fly was "knocked down" with humidified $CO_2$, passed briefly through a 70% ethanol (ETOH) bath, and then rinsed in deionized water; (b) the fly was placed on a clean glass slide in a drop of chilled 0.15M saline, the legs, wings and head were removed, and the thorax was split sagittally using a razor blade or scalpel; (c) the fly was then transferred to a fresh drop of chilled saline in a watch glass or a small dish filled with paraffin, and the two halves of the thorax were peeled back using minute dissecting needles; (d) using forceps, the abdominal cuticle was pulled away to expose the internal organs, the salivary glands were then teased away from the gut tissue, the anterior end of the gut (the cardia) was clipped, and the gut-salivary gland assembly was withdrawn by pulling it through the abdomen-thorax constriction; (e) the glands were then teased away from the gut, rinsed once in cold saline and transferred to an Eppendorf on ice during the collection process, and then frozen at −70° C.

Preparation of Salivary Gland Extracts

Salivary gland extracts (SGEs) were prepared by sonication. Sonic disruption of glands was obtained using 70% cycle and 70% power output of a Sonifier 450 (Branson Ultrasonics, Danbury, Conn.) by holding the tip of each tube to the base of the sonic probe immersed in an ice bath to disperse heat for 2 minutes. Salivary gland extracts were transferred to a new tube following removal of cell fragments by centrifugation at ≈12,000×g for 5 minutes at 4° C. The amount of protein per individual gland was determined using a BCA protein assay kit (Pierce, Rockford, Ill). Initial measurement of soluble protein obtained from sonicated *H. irritans* salivary glands was 0.54±0.09 μg/pair of glands for females and 0.63±0.02 μg/pair of glands for males.

Electrophoresis and Western Blotting

Figure 3:
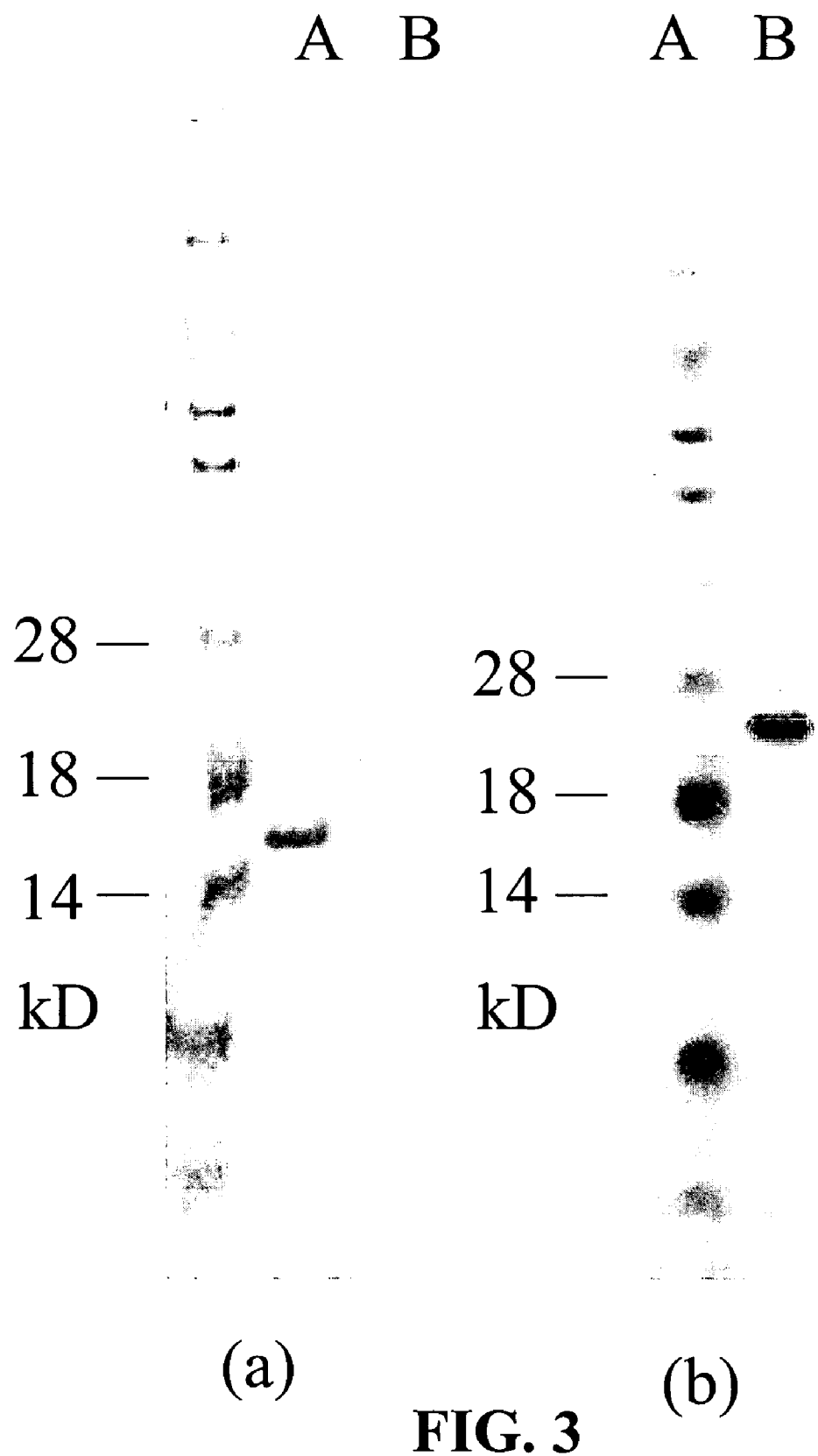
FIG. 3 shows an SDS-PAGE gel of recombinant haematollogen produced in Sf9 cells (gel a) and in *E. coli* (gel b) and purified with HPLC. Lane A of each gel shows markers, while lane B of each gel shows the haematollogen preparation.
Figure 4:
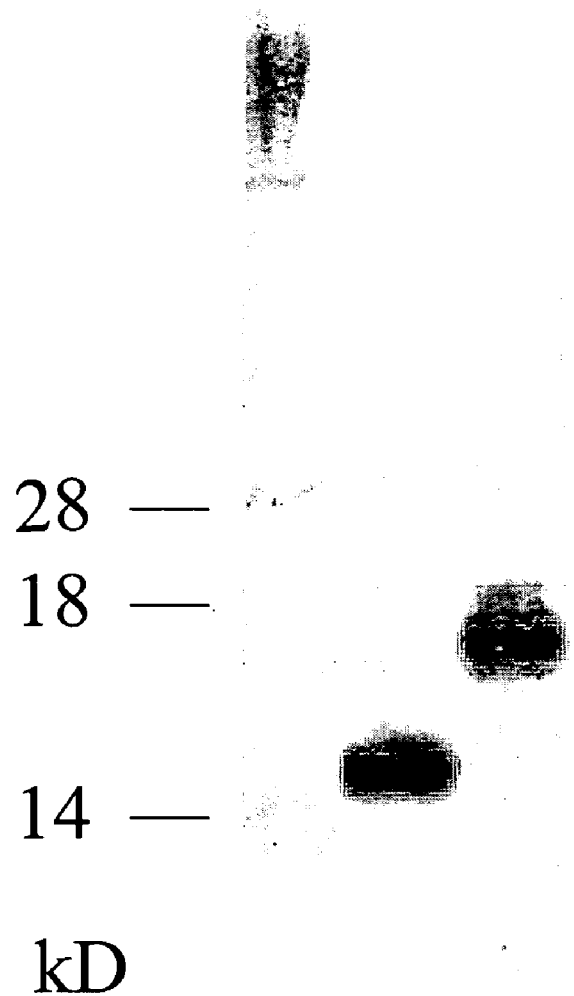
FIG. 4 shows a Western blot analysis of haematollogen using antibodies raised in a NZW rabbit immunized with haematollogen produced in *E. coli*. are shown in lane A, recombinant haematollogen is shown in lane B, and recombinant haematollogen with an 8× His-Tag is shown in lane C.

Proteins were resolved on 12% NuPAGE pre-cast gels (Invitrogen, Carlsbad, Calif.) and visualized using Simply-Blue SafeStain and the methods of the manufacturer (Invitrogen, Carlsbad, Calif.) (FIGS. 2 and 3). For antibody detection, proteins were transferred to Immun-Blot™ PVDF membranes (BIO-RAD, Hercules, Calif.) and developed with haematollogen-immunized rabbit antiserum and HRP-conjugated Goat anti-rabbit IgG (KPL Laboratories, Gaithersburg, Md.) (FIG. 4). A partial (N-terminal) amino acid sequence of the protein was then determined using standard techniques.

Example 2—Cloning and Expression of Haematollogen

Cloning

Salivary glands dissected from field-collected horn flies were used to isolate total RNA using a NucleoSpin RNA II kit (BD Biosciences Clontech). Two cDNA populations (5'-RACE-Ready cDNA and 3'-RACE-Ready cDNA) were generated with 1 μg of total RNA using SMART™ RACE cDNA Amplification kit (BD Biosciences Clontech). A 3'-RACE reaction was performed using 3'-RACE-Ready cDNA as template. Amplification primers that were gene-specific and degenerate were designed based on the partial amino acid sequence of the protein. The amplified DNA product, which resolved as a single band after agarose gel electrophoresis, was purified and directly sequenced. The 3'-end sequence was then used to design a reverse gene-specific primer, which was used to perform 5'-RACE using 5'-RACE-Ready cDNA as template. The resulting DNA product was sequenced and confirmed to correspond to the isolated protein; the apparent full-length gene was then cloned into pCR4-TOPO® vector (Invitrogen).

Expression of Haematollogen in Bacteria

A polynucleotide encoding the mature haematollogen protein (i.e., exclusive of the signal peptide) was subcloned into pTriEx™-4 expression cassette (Novagen). This cassette provides a sequence that encodes a His Tag comprising consecutive histidine residues so that a protein expressed using the vector will include the appended His Tag. The recombinant cassette was transferred into an *E. coli* expression host, Rosetta™ (Novagen). Transformed bacteria were cultured at 37° C. in LB medium supplemented with 1% glucose and antibiotics (50 μg/ml carbenicillin and 34 μg/ml chloramphenicol). Recombinant protein production was induced with IPTG (up to 300 μM). After 2 to 3 hours of induction at 37° C., cells were harvested by centrifugation and protein extraction was carried out in accordance with the BugBuster™ protein extraction protocol (Novagen). The target protein was purified using His.Bind™ resins from Novagen. Both soluble and insoluble fractions were analyzed with SDS-PAGE and Western blotting.

Haematollogen Expression in Insect Sf9 Cells.

The full-length haematollogen gene was cloned into the PstI and NotI sites of the pBacPAK8 plasmid (a transfer vector from Clontech). The target gene in the recombinant vector was then transferred in vivo into BacPAK6 (Clontech) viral genome according to the manufacturer's instruction. Recombinant viruses were isolated and amplified and then used to infect Sf9 host cells. Sf9 cells, in a monolayer, were infected at a multiplicity of infection of 10 in Insect-Xpress medium (a serum-free medium from BioWhittaker). Cell culture supernatant was harvested by centrifugation 72-hour post infection and frozen at −20° C.

Purification of Recombinant Haematollogen

Recombinant haematollogen produced by Sf9 cells was purified as follows. Sf9 cell culture supernatant was thawed and mixed with 80% $(NH_4)_2SO_4$ (w/v) in an ice bath. The mixture was centrifuged at 15,000×g at 4° C. for 30 minutes. The pellet was resuspended in de-ionized water and passed through a PD-10 column (Amersham Biosciences) to desalt. The eluted protein suspension was filtered through a 50,000-MWCO centrifugal filter device (Amicon® Ultra, Millipore®). The retentate was washed twice with 10 mM Tris (pH 8.0), and the filtrates were combined and concentrated with a 5,000-MWCO centrifugal device. The concentrated proteins were then separated and purified using reverse-phase HPLC with a Macrosphere C-18 column (300 Å, 5 μm, 250×10 mm, Alltech®) and gradient elution with solvents as follows: A: 20% acetonitrile (ACN) with 0.12% trifluoroacetic acid (TFA) and B: 60% ACN with 0.11% TFA. Aliquots of the collected fractions were lyophilized and analyzed by SDS-PAGE and Western blot. Aliquots of the putative target fractions were co-lyophilized with 1% BSA solution (which resulted in 0.1% BSA in solution after reconstitution). Recombinant haematollogen produced in Sf9 cell culture was purified to near homogeneity by the methods applied, as indicated by SDS-PAGE and Western analyses (FIG. 3).

Haematollogen Gene Structure

The reconstructed cDNA encoding haematollogen (SEQ ID NO:3) encoded a protein product 148 amino acids in length (SEQ ID NO:4) (also shown in FIG. 1). The amino acid sequence of the mature protein purified from salivary glands (SEQ ID NO:2) began with phenylalanine (the $21^{st}$ residue encoded by the translated cDNA), so the first 20 amino acids of the sequence set forth in SEQ ID NO:4 are likely to be a signal peptide. In addition, in the reconstructed cDNA, the haematollogen coding region was flanked by a 51-bp untranslated sequence at the 5'-end preceding the initial ATG start codon and a 63-bp untranslated sequence at the 3'-end prior to the poly-A tail. The secreted haematollogen protein has a calculated molecular mass of 14.4 kDa with an isoelectric point (pI) of 7.82. BLAST searches of nucleotide and amino acid sequence databases maintained by NCBI (the National Center for Biotechnology Information) found no significant sequence similarity with any previously-known sequences.

Production of Haematollogen in E. coli

When expressed in an E. coli host, haematollogen fusion protein (i.e., haematollogen protein with an N-terminal His Tag) was present only in inclusion bodies of induced E. coli (FIG. 2). The inclusion bodies were isolated from E. coli cell extracts and resuspended in 1× His•Bind binding buffer (5 mM imidazole, 50 mM NaCl, 20 mM Tris-HCl, pH 7.9) including 6 M urea. Upon His•Bind column purification, the fusion haematollogen was eluted in a buffer containing 6 M urea, 1 M imidazole, 0.5 M NaCl, and 20 mM Tris-HCl, pH 7.9. A final buffer exchange and protein concentration were carried out using a 5,000-MWCO centrifugal device and a buffer composed of 50 mM Tris-HCl (pH 7.9), 100 mM NaCl, and 6 M urea. The resulting haematollogen fusion protein was estimated to be more than 90% pure by SDS-PAGE (FIG. 3).

Example 3—Production of Antibodies

A New Zealand White rabbit was immunized by injection at 5 sites intradermally and 5 sites subcutaneously with a total of 50 μg of recombinant haematollogen which had been expressed in the Rosetta strain of E. coli as described above and then emulsified in Freund's Complete Adjuvant (FCA). Two immunization boosts of 50 μg recombinant haematollogen, emulsified in Freund's Incomplete Adjuvant (IFA), were injected at 4 sites intramuscularly on days 14 and 35 after the initial priming injection. This procedure resulted in the production of antibodies that bind to haematollogen, as confirmed by Western blotting (see FIG. 4).

Example 4—Efficacy of Haematollogen as a Veterinary Vaccine

Vaccination experiments were performed on four pairs of calves that were matched by age. Test calves were immunized with a priming dose of 50 μg of purified haematollogen emulsified in complete Freund's adjuvant and injected in equal parts into six sites—three intradermal and three subcutaneous. Calves were then "boosted" twice. with 50 μg protein each; the protein was emulsified in Freund's incomplete adjuvant and injected in equal parts into four sites subcutaneously. Control calves were immunized with ovalbumin (OVA) protein using the same procedure. Two or more weeks after the second boost, calves were exposed to hematophagous flies by attaching a feeding cage containing 20 flies to a shaved area of the skin on the dorsal side of the calf. Each group of calves was tested three times.

The volume of blood obtained by the feeding flies was determined by a quantitative measurement of hemoglobin within the midgut (Cupp et al. (2004) Vaccine 22: 2285–2297). The tendency was for flies fed on haematollogen-immunized calves to obtain less blood from the calf, although the p-value obtained from the experiment was 0.06, and differences among groups were also significant.

The degree of development of ovarioles in the hematophagous flies was scored after 24, 48, and 72 hours of continuous exposure of flies to a test or control calf. The number of ovarioles showed a significant decrease (p=0.015) in test calves versus control calves, although differences among groups were significant.

Example 5—Effect of Recombinant Haematillogen on Collagen I-Induced Platelet Aggregation Recombinant SVEP ("rSVEP" control; see, e.g., U.S. Pat. No. 6,162,785) and haematollogen ("HFX") proteins were expressed in vitro by Sf9 cells infected with recombinant baculoviruses BV/SVEP or BV/HFX. Culture supernatants collected at 72 hours post-infection were processed with sequential centrifugation using 100 and 10 kDA cutoff membranes (Centricon Plus 20, Millipore Corporation, Bedford, Mass.) that yielded concentrated, semi-pure preparations ($10\ kDa \leq x \leq 100\ kDa$).

The ability of this semi-purified, recombinant haematollogen to inhibit the aggregation response of bovine platelets to collagen I was tested in an in vitro kinetic assay as described by Krause et al. (2001) Platelet 12: 423–430, herein incorporated by reference. Briefly, platelet aggregation testing was carried out in 96-well, flat-bottomed microtiter plates. Samples of platelet-rich plasma were placed in the microtiter plate. Then, aliquots of test and control proteins were added to the samples directly before the reading was started. Measurements of the optical density were performed at 650 nm. During the run time the plate was incubated at 37° C. and was mixed intermittently. Results are shown below in Table 1. In both samples used in each test, the collagen concentration was 3 μg/ml and the volume ($10\ kDa \leq x \leq 100\ kDa$) was 10 μl.

The rate value is a measure of decrease in light absorbance with time which occurs when platelets in suspension become aggregated in response to the addition of collagen. The presence of recombinant haematollogen significantly decreases the aggregation response compared to a similar preparation with the control protein, rSVEP.

TABLE 1

| Test | Recombinant Protein | n = | Rate (mean ± SD) | p = |
|---|---|---|---|---|
| 1 | rSVEP | 4 | −5.809 ± 0.538 | 0.0001 |
| | rHFX | 4 | −1.751 ± 0.262 | |
| 2 | rSVEP | 7 | −5.659 ± 0.653 | 0.0001 |
| | rHFX | 8 | −1.613 ± 0.301 | |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Other modifications and embodiments of the invention will come to mind in one skilled in the art to which this invention pertains having the benefit of the teachings presented herein. Therefore, it is to be understood that the invention is not to be limited to the specific embodiments disclosed. Although specific terms are employed, they are used in generic and descriptive sense only and not for purposes of limitation, and that modifications and embodiments are intended to be included within the scope of the appended claims.

That which is claimed:

1. A purified protein comprising the amino acid sequence set forth in SEQ ID NO: 2, wherein said protein disrupts platelet aggregation.

2. The protein of claim 1, wherein said protein is produced by recombinant methods.

3. A pharmaceutical composition comprising an amount of the protein of claim 1 that is therapeutically effective for disrupting platelet aggregation.

4. A veterinary vaccine comprising a therapeutically effective amount of the protein of claim 1.

5. A method of treating hematophagy of cattle, said method comprising administering to said cattle the vaccine of claim 4.

6. A method of treating a mammal for a condition in which decreased platelet aggregation would be beneficial, said method comprising administering to said mammal a therapeutically effective amount of a protein that disrupts platelet aggregation, wherein said protein comprises the amino acid sequence of SEQ ID NO: 2.

7. The method of claim 6, wherein said protein is produced by recombinant methods.

* * * * *

UNITED STATES PATENT AND TRADEMARK OFFICE
CERTIFICATE OF CORRECTION

PATENT NO. : 7,211,652 B2 Page 1 of 1
APPLICATION NO. : 10/996248
DATED : May 1, 2007
INVENTOR(S) : Cupp et al.

It is certified that error appears in the above-identified patent and that said Letters Patent is hereby corrected as shown below:

On Title Page
Item (56) References Cited,
FOREIGN PATENT DOCUMENTS: "WO     98/04795     3/1998"
    should read     --WO     WO 98/40089     3/1998--

Signed and Sealed this

Seventh Day of August, 2007

JON W. DUDAS
*Director of the United States Patent and Trademark Office*

```
                              SEQUENCE LISTING

<160> NUMBER OF SEQ ID NOS: 4

<210> SEQ ID NO 1
<211> LENGTH: 384
<212> TYPE: DNA
<213> ORGANISM: Haemotobia irritans

<400> SEQUENCE: 1
ttcaatcctt ttggcgcagg aggtcttagt gtagacgtca ccgataaaca attcaaatgc      60
gacaagatct cttgtcccgc tgataccgaa cgttgtgtag ttagcacgga aaaagatccc     120
agaaatccta gaatcctggc tcacaccaac ctctgtctct cacgcaccgg ttcagtgttg     180
gaaaagaaga catggtacga aagcaccttt aaaaagcaaa aggttaatgt acacattgat     240
gcctatcgct atgaaggaaa attcacacct caagttttag caaacaactg ggatgccgga     300
aaaattgatg ccggaaaaac tgctaaggag gacaatgatg cattcaatag agctgtcgaa     360
gaacttagca agagtttaga cttt                                            384

<210> SEQ ID NO 2
<211> LENGTH: 128
<212> TYPE: PRT
<213> ORGANISM: Haemotobia irritans

<400> SEQUENCE: 2

Phe Asn Pro Phe Gly Ala Gly Gly Leu Ser Val Asp Val Thr Asp Lys
 1               5                  10                  15

Gln Phe Lys Cys Asp Lys Ile Ser Cys Pro Ala Asp Thr Glu Arg Cys
            20                  25                  30

Val Val Ser Thr Glu Lys Asp Pro Arg Asn Pro Arg Ile Leu Ala His
        35                  40                  45

Thr Asn Leu Cys Leu Ser Arg Thr Gly Ser Val Leu Glu Lys Lys Thr
    50                  55                  60

Trp Tyr Glu Ser Thr Phe Lys Lys Gln Lys Val Asn Val His Ile Asp
65                  70                  75                  80

Ala Tyr Arg Tyr Glu Gly Lys Phe Thr Pro Gln Val Leu Ala Asn Asn
                85                  90                  95

Trp Asp Ala Gly Lys Ile Asp Ala Gly Lys Thr Ala Lys Glu Asp Asn
            100                 105                 110

Asp Ala Phe Asn Arg Ala Val Glu Glu Leu Ser Lys Ser Leu Asp Phe
        115                 120                 125
```

<210> SEQ ID NO 3
<211> LENGTH: 592
<212> TYPE: DNA
<213> ORGANISM: Haemotobia irritans

<400> SEQUENCE: 3

```
gaaccatttc tctcgagaca tcccaagtga tacctaacac aattcctcat aatggctatc      60
aaaatcttga cagttctttt ggttgttagc tgtttgagct atgcctatgg tttcaatcct     120
tttggcgcag gaggtcttag tgtagacgtc accgataaac aattcaaatg cgacaagatc     180
tcttgtcccg ctgataccga acgttgtgta gttagcacgg aaaagatcc cagaaatcct     240
agaatcctgg ctcacaccaa cctctgtctc tcacgcaccg gttcagtgtt ggaaagaag     300
acatggtacg aaagcacctt taaaaagcaa aaggttaatg tacacattga tgcctatcgc     360
tatgaaggaa aattcacacc tcaagtttta gcaaacaact gggatgccgg aaaaattgat     420
gccggaaaaa ctgctaagga ggacaatgat gcattcaata gagctgtcga agaacttagc     480
aagagtttag acttttaaaa tggaataaat tcttttgtga agcgatcgct taatatgttg     540
tcattgtgta atgaatgcaa ataaataaat aaaaaaaatc agcataacaa aa             592
```

<210> SEQ ID NO 4
<211> LENGTH: 148
<212> TYPE: PRT
<213> ORGANISM: Haemotobia irritans

<400> SEQUENCE: 4

```
Met Ala Ile Lys Ile Leu Thr Val Leu Leu Val Val Ser Cys Leu Ser
 1               5                  10                  15

Tyr Ala Tyr Gly Phe Asn Pro Phe Gly Ala Gly Gly Leu Ser Val Asp
             20                  25                  30

Val Thr Asp Lys Gln Phe Lys Cys Asp Lys Ile Ser Cys Pro Ala Asp
         35                  40                  45

Thr Glu Arg Cys Val Val Ser Thr Glu Lys Asp Pro Arg Asn Pro Arg
     50                  55                  60

Ile Leu Ala His Thr Asn Leu Cys Leu Ser Arg Thr Gly Ser Val Leu
 65                  70                  75                  80

Glu Lys Lys Thr Trp Tyr Glu Ser Thr Phe Lys Lys Gln Lys Val Asn
                 85                  90                  95

Val His Ile Asp Ala Tyr Arg Tyr Glu Gly Lys Phe Thr Pro Gln Val
            100                 105                 110

Leu Ala Asn Asn Trp Asp Ala Gly Lys Ile Asp Ala Gly Lys Thr Ala
        115                 120                 125

Lys Glu Asp Asn Asp Ala Phe Asn Arg Ala Val Glu Glu Leu Ser Lys
    130                 135                 140

Ser Leu Asp Phe
145
```